US010604814B2

(12) United States Patent
Lee et al.

(10) Patent No.: US 10,604,814 B2
(45) Date of Patent: Mar. 31, 2020

(54) MANUFACTURING PROCESS CONTROL WITH DEEP LEARNING-BASED PREDICTIVE MODEL FOR HOT METAL TEMPERATURE OF BLAST FURNACE

(71) Applicant: International Business Machines Corporation, Armonk, NY (US)

(72) Inventors: Young Min Lee, Old Westbury, NY (US); Kyong Min Yeo, Scarsdale, NY (US)

(73) Assignee: International Business Machines Coporation, Armonk, NY (US)

( * ) Notice: Subject to any disclaimer, the term of this patent is extended or adjusted under 35 U.S.C. 154(b) by 238 days.

(21) Appl. No.: 15/716,794

(22) Filed: Sep. 27, 2017

(65) Prior Publication Data

US 2019/0093186 A1     Mar. 28, 2019

(51) Int. Cl.
| | | |
|---|---|---|
| *C21B 7/06* | (2006.01) | |
| *G01B 21/08* | (2006.01) | |
| *G01K 17/20* | (2006.01) | |
| *G01K 7/04* | (2006.01) | |
| *G01K 3/04* | (2006.01) | |

(Continued)

(52) U.S. Cl.
CPC ............. *C21B 7/06* (2013.01); *C21B 5/006* (2013.01); *G01B 21/085* (2013.01); *G01K 3/04* (2013.01); *G01K 7/04* (2013.01); *G01K 7/42* (2013.01); *G01K 17/20* (2013.01); *G06N 3/00* (2013.01); *G06N 20/00* (2019.01);

(Continued)

(58) Field of Classification Search
CPC ... C21B 7/06; G01K 7/42; G01K 7/04; G01N 25/18; G01N 25/72
See application file for complete search history.

(56) References Cited

U.S. PATENT DOCUMENTS 5,975,754 A    11/1999   Groth et al.

FOREIGN PATENT DOCUMENTS

| CN | 101457268 A | 6/2009 |
|---|---|---|
| CN | 103160629 A | 6/2013 |

(Continued)

OTHER PUBLICATIONS

Jimenez, J., et al., "Blast Furnace Hot Metal Temperature Prediction through Neural Networks-Based Models", ISIJ International, pp. 573-580, vol. 44, No. 3, Jun. 4, 2004. (Year: 2004).*

(Continued)

*Primary Examiner* — Matthew D Krcha
(74) *Attorney, Agent, or Firm* — Scully, Scott, Murphy & Presser, P.C.; Daniel P. Morris

(57) ABSTRACT

A blast furnace control system may include a hardware processor that generates a deep learning based predictive model for forecasting hot metal temperature, where the actual measured HMT data is only available sparsely, and for example, measured at irregular interval of time. HMT data points may be imputed by interpolating the HMT measurement data. HMT gradients are computed and a model is generated to learn a relationship between state variables and the HTM gradients. HMT may be forecasted for a time point, in which no measured HMT data is available. The forecasted HMT may be transmitted to a controller coupled to a blast furnace, to trigger a control action to control a manufacturing process occurring in the blast furnace.

13 Claims, 11 Drawing Sheets

(51) Int. Cl.
*G01K 7/42* (2006.01)
*G06N 20/00* (2019.01)
*C21B 5/00* (2006.01)
*G06N 3/00* (2006.01)
G01N 25/72 (2006.01)
G01N 25/18 (2006.01)

(52) U.S. Cl.
CPC .......... *C21B 2300/04* (2013.01); *G01N 25/18* (2013.01); *G01N 25/72* (2013.01)

(56) References Cited

FOREIGN PATENT DOCUMENTS

| CN | 104298214 A | 1/2015 |
| CN | 106681146 A | 5/2017 |
| JP | 02170904 A | 7/1990 |
| JP | 03104808 A | 5/1991 |
| JP | 2002317217 A | 10/2002 |
| JP | 101457268 A | 6/2009 |

OTHER PUBLICATIONS

Cantera, C., et al., "Predicción mediante redes neuronales de la temperatura de arrabio de un horno alto. Temperatura subyacente de arrabio", Revista de Metalurgia, pp. 243-248, vol. 38, 2002 (Year: 2002).*

List of IBM Patents or Patent Applications Treated as Related, dated Nov. 15, 2017, 2 pages.

Zhou, P., et al., "Data-Driven Nonlinear Subspace Modeling for Prediction and Control of Molten Iron Quality Indices in Blast Furnace Ironmaking", IEEE Transactions on Control Systems Technology, Sep. 2017, pp. 1761-1774, vol. 25, No. 5.

Qiu, D., et al., "AN application of prediction model in blast furnace hot metal silicon content based on neural network", International Conference on Apperceiving Computing and Intelligence Analysis, Oct. 2009, pp. 61-64.

Jimenez, J., et al., "Blast Furnace Hot Metal Temperature Prediction through Neural Networks-Based Models", ISIJ International, pp. 573-580, vol. 44, No. 3, Jun. 4, 2004.

Yue, Y., et al., "Study on Prediction Model of Blast Furnace Hot Metal Temperature", Proceedings of the 2016 IEEE International Conference on Mechatronics and Automation, Aug. 7-10, 2016, pp. 1396-1400.

Yikang, W., et al., "Modeling hot metal silicon content in blast furnace based on locally weighted SVR and mutual Information", Proceedings of the 31st Chinese Control Conference, Jul. 25-27, 2012, pp. 7089-7094.

Lasko, T.A., et al. "Computational Phenotype Discovery Using Unsupervised Feature Learning over Noisy, Sparse, and Irregular Clinical Data", PLOS ONE, Published Jun. 24, 2013, 13 pages, vol. 8, Issue 6.

Lipton, Z.C., et al., "Modeling Missing Data in Clinical Time Series with RNNs", Proceedings of Machine Learning for Healthcare 2016, Nov. 11, 2016, 17 pages, JMLR W&C Track vol. 56.

Che, Z., et al., "Recurrent Neural Networks for Multivariate Time Series with Missing Values", https://arxiv.org/pdf/1606.01865.pdf, Nov. 7, 2016, Accessed Sep. 27, 2016, 14 pages.

Hochreiter, S., et al., "Long Short-Term Memory", Neural Computation, Nov. 15, 1997, 32 pages, vol. 9, Issue 8.

Lecun,. Y., et al., "Deep learning", Nature, May 28, 2015, pp. 436-444, vol. 521.

Radhakrishnan, M., et al., "Neural networks for the identification and control of blast furnace hot metal quality," Journal of Process Control, Dec. 2000, pp. 509-524, vol. 10, Issue 6.

Zeng , J.-S., et al., "Data-driven predictive control for blast furnace ironmaking process", Computers and Chemical Engineering, Available online Jan. 15, 2010, pp. 1854-1862, vol. 34.

\* cited by examiner

MANUFACTURING PROCESS CONTROL WITH DEEP LEARNING-BASED PREDICTIVE MODEL FOR HOT METAL TEMPERATURE OF BLAST FURNACE

FIELD

The present application relates to an apparatus and control system for a manufacturing process.

BACKGROUND

A steel manufacturing process using a blast furnace is a complex, continuous operation that involves multiple chemical reactions and phase transitions of materials. To better control the blast furnace during the manufacturing process for continuous production of quality metals, it is useful to be able to predict state variables in the future time associated with the production such as the temperature of the hot metal produced by the blast furnace. Generally, prediction algorithms utilize historical data for predicting the future data. However, in steel manufacturing process involving the blast furnace, the state variables such as the hot metal temperature (also referred to as the pig iron temperature) are measured sparsely, for example, once in every few hours at an irregular interval. Sparse, irregular measurement data makes it difficult to be able to accurately predict the future data.

Other examples of continuous manufacturing processes include the aluminum smelting process, in which temperature of aluminum bath is measured once in two days, and the cement manufacturing process measuring fineness of cement particles once in an hour in a grinding station.

BRIEF SUMMARY

A blast furnace control system and a method of controlling a manufacturing process in a blast furnace may be provided. The blast furnace control system, in one aspect, may include a storage device storing a database of manufacturing process data associated with a blast furnace. A hardware processor may be coupled to the storage device and operable to receive the manufacturing process data, the manufacturing process data may include state variables and control variables used in operating the blast furnace, the state variables comprising at least a hot metal temperature (HMT) and other state variables. The manufacturing process data may include a plurality of measured HMT at different time points, of a product continuously produced in the blast furnace. The hardware processor may be further operable to generate imputed HMT by interpolating the plurality of measured HMT. The hardware processor may be further operable to generate HMT gradients over time at least based on the imputed HMT. The hardware processor may be further operable to define a causal relationship between the other state variables and the HMT gradients, the relationship generated as a neural network model. The hardware processor may be further operable to train the neural network model using as training data, a weighted combination of the imputed HMT up to last known measured HMT and predicted HMT up to the last known measured HMT. The hardware processor may be further operable to run the trained neural network model to predict a current point in time value for the HMT, in which no measured HMT for the current point in time is available, wherein the trained neural network model predicts the HMT corresponding to a time period starting from the time of the last measured HMT for a number of time periods until the number of time periods advances to the current point in time and use the predicted HMT corresponding to each of the number of time periods to predict the current point in time value for the HMT. The hardware processor may be further operable to transmit the current point in time value for the HMT to a controller, the controller coupled to the blast furnace operable to trigger a control action to control a manufacturing process occurring in the blast furnace.

A method of controlling a manufacturing process in a blast furnace, in one aspect, may include receiving manufacturing process data associated with a blast furnace. The manufacturing process data may include state variables and control variables used in operating the blast furnace, the state variables comprising at least a hot metal temperature (HMT) and other state variables. The manufacturing process data may include a plurality of measured HMT at different time points, of a product continuously produced in the blast furnace. The method may also include generating imputed HMT by interpolating the measured HMT. The method may further in clued generating HMT gradients based on at least the imputed HMT. The method may also include defining a causal relationship between the other state variables and the HMT gradients, the relationship generated as a neural network model. The method further include training the neural network model using as training data, a weighted combination of the imputed HMT up to a last known measured HMT and predicted HMT up to the last known measured HMT. The method may further include running the trained neural network model to predict a current point in time value for the HMT, in which no measured HMT for the current point in time is available, wherein the trained neural network model predicts the HMT corresponding to a time period starting from the time of the last measure HMT data point for a number of time periods until the number of time periods advances to the current point in time and uses the predicted HMT corresponding to each of the number of time periods to predict the current point in time value for the HMT. The method may also include transmitting the current point in time value for the HMT to a controller coupled to the blast furnace, to trigger a control action to control a manufacturing process occurring in the blast furnace.

A computer readable storage medium storing a program of instructions executable by a machine to perform one or more methods described herein also may be provided.

Further features as well as the structure and operation of various embodiments are described in detail below with reference to the accompanying drawings. In the drawings, like reference numbers indicate identical or functionally similar elements.

DETAILED DESCRIPTION

A control system, apparatus, method and techniques are disclosed that develop a deep learning (DL)-based predictive model for a manufacturing process, where available measurement data for state variables are sparse, to be able to control the manufacturing process. A predictive model in one embodiment predicts one or more state variables using machine learning (ML) or deep learning (DL). The DL-based predictive model in one embodiment is a data-driven model that is trained based on sparse observations (measurements) of one or more state variables.

In blast furnace operation, measurement data for state variables such as the hot metal temperature data are available only sparsely. A DL-based predictive model in one embodiment predicts the hot metal temperature (HMT) of blast furnace operation with sparsely measured hot metal temperature data.

For example, one or more of ML and DL techniques are employed to develop a predictive model that can predict status of a manufacturing process, a blast furnace operation of steel manufacturing process. A blast furnace involves a complex operation that includes multiple chemical reactions and phase transitions of materials, which are difficult to model using first principle equations. At the same time, because of the complex multi-scale nature of the process, in which the response time of the input materials, such as iron ore, coke, oxygen, water, pulverized coal (PC), have wide variations from order of minutes to hours, it is difficult to develop a data-driven model in the conventional machine-learning approaches. In one embodiment of the present disclosure, a time-series prediction DL model, called Recurrent Neural Network (RNN), is employed to build a predictive model. Particularly, an embodiment of the present disclosure may use the Long Short-Term Memory (LSTM) network, which is capable of learning multi-scale temporal dependency structures, to build models for predicting state variables (e.g., key state variables) of the blast furnace operation. The LSTM is able to capture complex non-linear dynamics well and is shown to outperform conventional ML algorithms, such as Sparse Linear Model (LASSO), Decision Tree, Gradient Boosting, and Gaussian Processes, in the prediction of blast furnace status.

Figure 1:
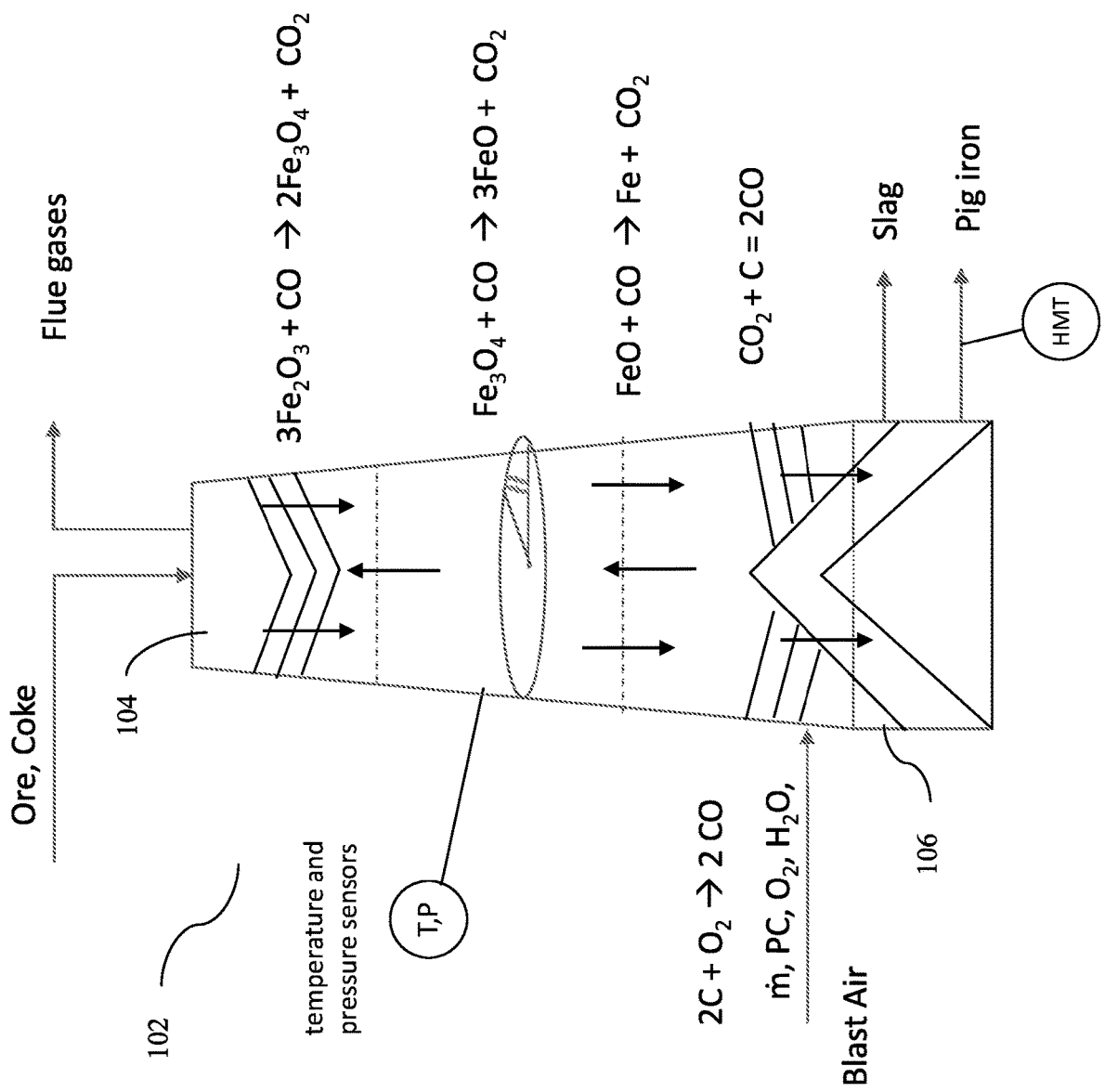
FIG. 1 is a diagram illustrating a blast furnace in one embodiment.

FIG. 1 is a diagram illustrating a blast furnace in one embodiment. A blast furnace 102 is a stack in which raw material such as iron ore and coke are deposited into the top 104 and preheated air with moisture and oxygen content and pulverized coal (PC) are input into the bottom 106. The blast furnace is also equipped with sensors that surround the blast furnace that measure various data, such as temperature and pressure, of the blast furnace in operation. A blast furnace in steel manufacturing process involves a complex, non-linear and continuous operation that includes multiple chemical reactions, phase transitions, and multiple phase interactions of materials. The process occurring in the blast furnace is difficult to model using first principle equations. Changes in input materials (such as iron ore, coke, oxygen, pulverized coal) have delayed impact on the process and the product quality. For instance, it takes about 6-8 seconds for blasted air to react with the materials and ascend to the top, and the raw materials or input materials take about 6-8 hours to descend to the bottom of the furnace, and become the final product such as slag and pig iron.

The blast furnace is operated in extreme conditions (e.g., temperature of approximately 2000 degrees Celsius, and atmospheric pressure of approximately 4 standard atmosphere (atm)), and the measurement condition for internal blast furnace conditions is hostile. There may be hundreds of process variables (e.g., temperature, pressure, raw material charge and exit) that are monitored and stored, for example, by the sensors. For instance, temperature sensors and pressure sensors may be coupled to or embedded on the surface of the blast furnace that measure the temperature and pressure of the blast furnace at different locations. At the raw material charge and the exit of the tap hole, sensors may be coupled that measure the input and output rates. The hot metal temperature (HMT) of the pig iron that is produced (output from the bottom of the blast furnace) is measured, for example, at intervals of time.

The operation of the blast furnace consumes a large amount of energy and emits a large amount of carbon dioxide ($CO_2$). A control objective of the blast furnace iron-making process is to keep the operation close to the optimal level, i.e., desired pig iron quality, low energy consumption and high production. A goal, for example, is to achieve a stable operation that achieves a desired blast furnace state and high quality pig iron, at low energy cost. The desired blast furnace state, for instance, includes balanced profiles of pressure and temperature, material (e.g., ore and coke) descending speed, gas permeability inside blast furnace, hot metal temperature, and Silicon (Si)/Phosphate (P)/Sulfate (S) content of pig iron. Ability to control the hot metal temperature (HMT), also called pig iron temperature, to be maintained approximately at 1,500 degrees Celsius is also desirable.

Figure 2:
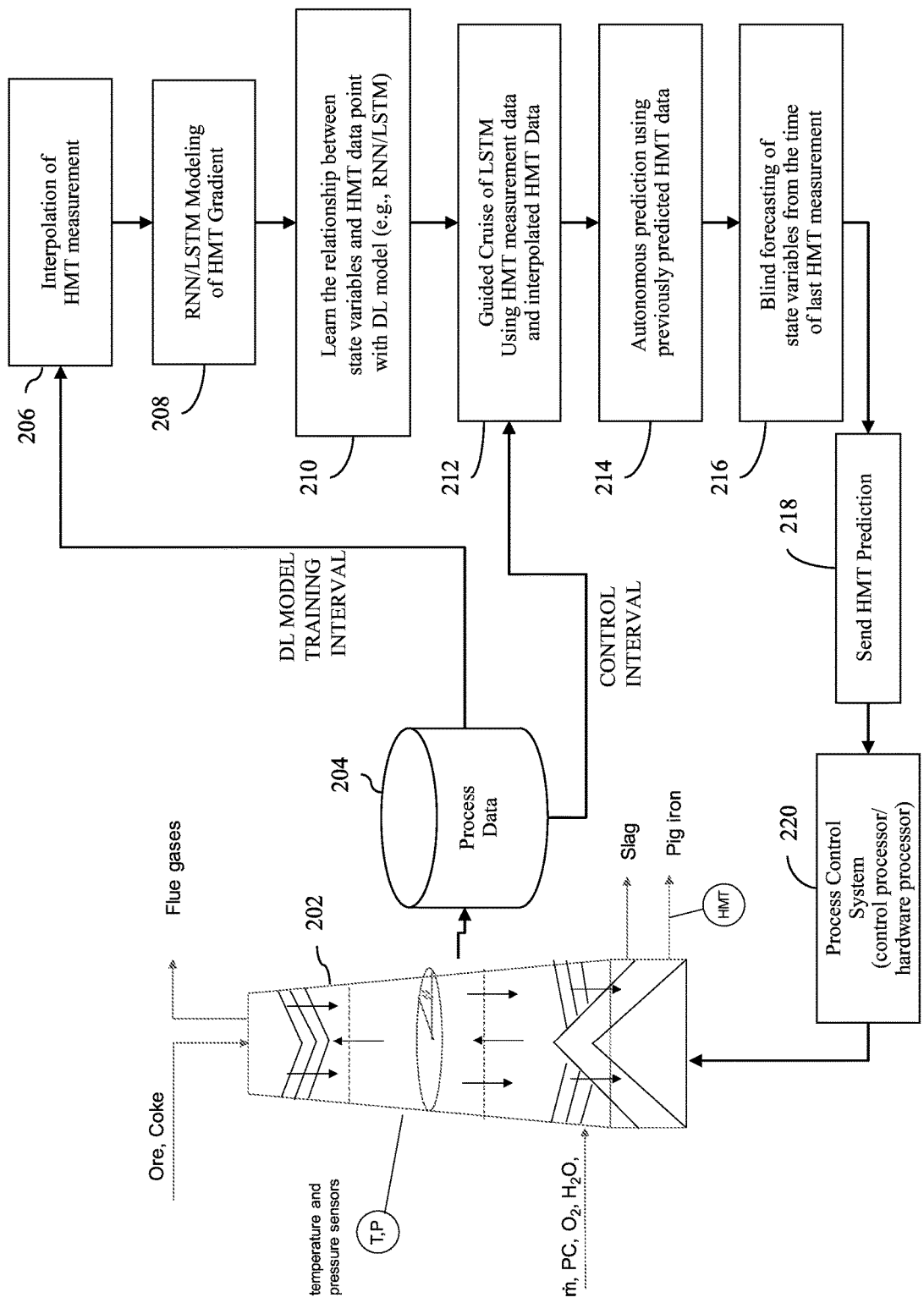
FIG. 2 is a diagram illustrating components of a control system in one embodiment.

FIG. 2 is a diagram illustrating components and processing flow of a control system in one embodiment. A computer or hardware processor coupled to a blast furnace 202 (and/or to a control system that controls the blast furnace 202) may perform the processing described below.

A database 204 of process data stores the manufacturing process data received from the sensors coupled to the blast furnace. The process data stored in the database may include the temperature, pressure, raw material charge rate, and air blow rate, measured periodically or at intervals of time. The process data other than the HMT is available more frequently than the HMT data, as measurements for HMT are performed less frequently, i.e., sparsely. For example, HMT data may be measured every 2-3 hours while other process data are measured every minute.

Figure 3:
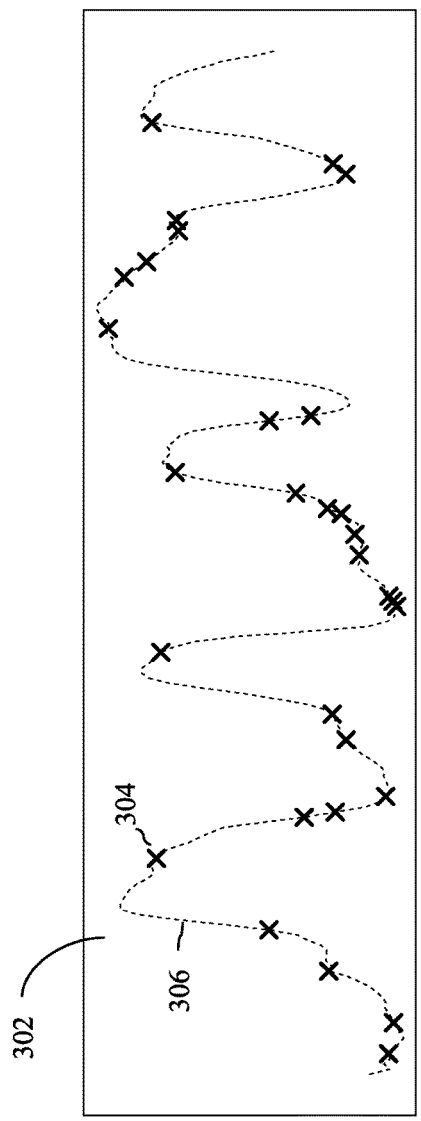
FIG. 3 is a diagram that illustrates an example of sparse measurement of a target variable as compared to other variables in one embodiment.

FIG. 3 is a diagram that illustrates an example of sparse measurement of a target variable as compared to other variables. The target variable, for example, hot metal temperature (HMT) is measured at an irregular interval (e.g., 2-4 hours), as shown by 'x' marks 304 in the graph 302, while the true state of HMT, as shown by dots 306 is not observed. With such data, it is difficult to apply conventional time series models, which assumes that there exists a continuous observation, i.e., the conventional models require $Y_t$ to predict $Y_{t+1}$.

Figure 4:
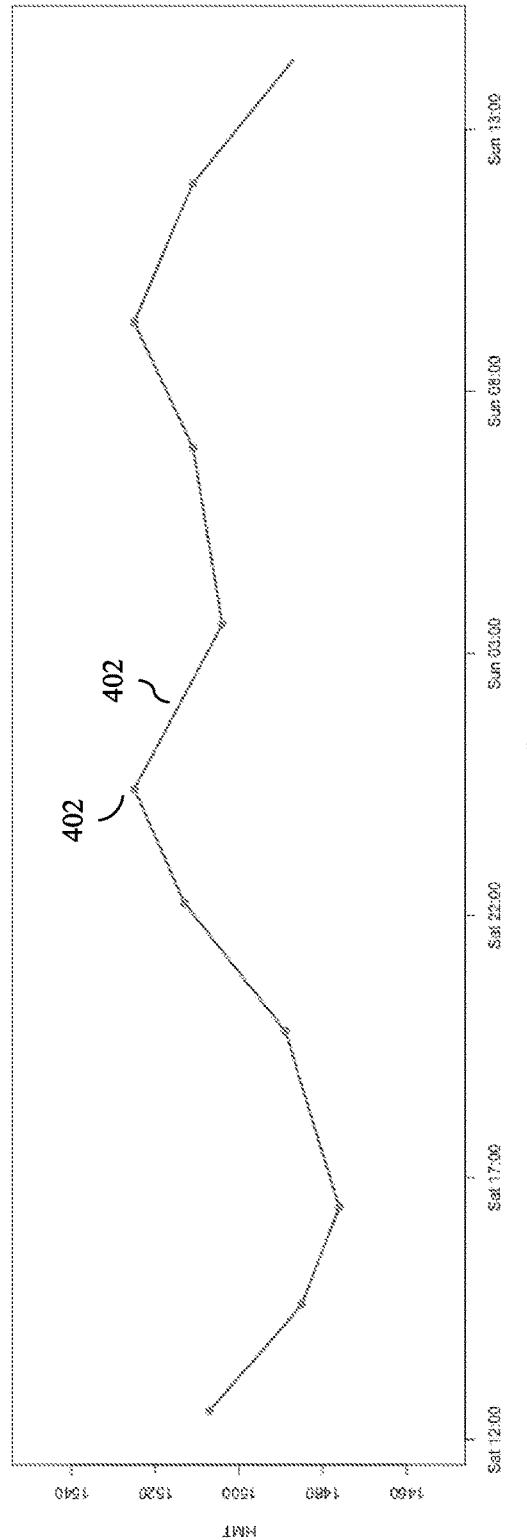
FIG. 4 shows a linear interpolation of HMT measurement data in one embodiment.

Referring to FIG. 2, the process data stored in the database 204 is received by a hardware processor. At 206, HMT data points are imputed by interpolating HMT measurement data. Interpolating the HMT measurement data produces additional data points between the actual measurement data for the HMT. FIG. 4 shows a linear interpolation of HMT measurement data in one embodiment. The dots (e.g., 402) represent the actual measured data. The data points (e.g., 404) between the dots are interpolated data. For example, about 80 percent (%) of the training data may comprise the linearly interpolated data and about 20% of the training data may comprise the real observations (actual measured data).

Figure 5B:
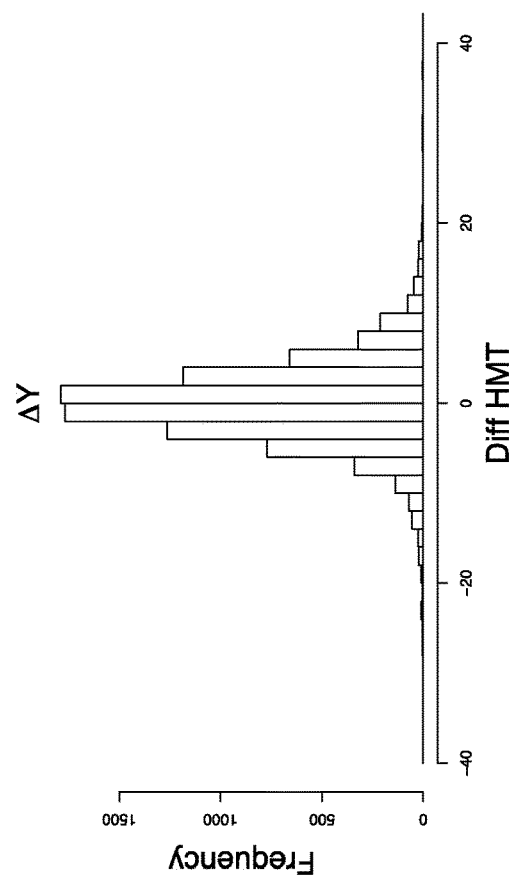
FIGS. 5A and 5B illustrate HMT distribution and HMT difference (delta) distribution in one embodiment.
Figure 5A:
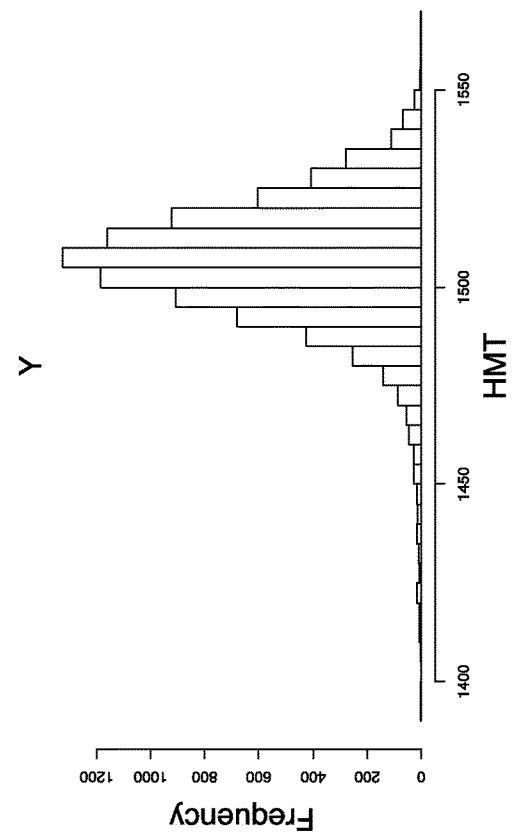
Figure 6:
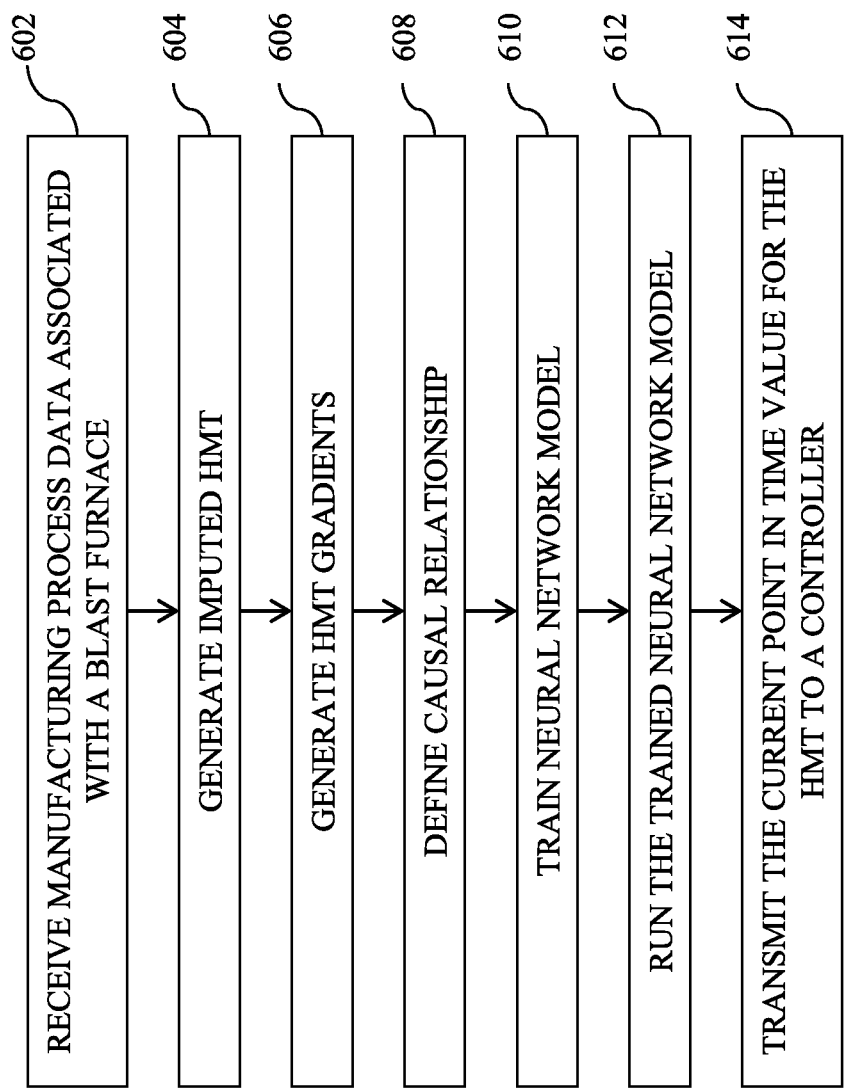
FIG. 6 is a diagram illustrating a method of controlling a manufacturing process occurring in a blast furnace in one embodiment of the present disclosure.

Referring to FIG. 2, at 208, a Recurrent Neural Network (RNN) Long Short-Term Memory (LSTM) modeling of HMT gradient is performed. For instance, HMT gradients are computed from the interpolated HMT data points. The gradient is defined by the difference of HMT at successive time steps, i.e., $dY_{t+1}=Y_{t+1}-Y_t$. Here, d represents delta, Y represents a state variable such as the HMT, and t represents time unit. In this modeling process, neural network architecture is set up. Prediction of $dY_{t+1}$, instead of $Y_{t+1}$, prevents a development of a short-circuit, in which RNN simply memorizes $Y_t$ and copies it to predict $Y_{t+1}$ as $Y_{t+1}=Y_t$, instead of learning the dynamics. FIGS. 5A and 5B illustrate HMT distribution and HMT difference (delta) distribution. The HMT distribution shown in FIG. 5A is skewed to the left, while the difference in HMT shown in FIG. 5B has a more symmetric distribution. The gradient of HMT is modeled by LSTM, a deep neural network, for example, as shown in FIG. 6. As explained above, there is no explicit short-cut to the previous prediction, e.g., RNN cannot copy the input Yt to make a prediction. In one embodiment, the LSTM model has a weighted $L_2$ loss function as follows:

$$L=\Sigma_{i=1}^N \Sigma_{j=1}^M (|dY_j^i|+\delta)^2 (dY_j^i - d\tilde{Y}_j^i)^2, \delta>0$$

Here, N is the number of total time series, M is the length of a time series, $dY_j^i$ denotes Y at the j-th time step for the i-th time series, $\tilde{Y}$ is the RNN prediction, and $\delta$ is a parameter. The weighted $L_2$ loss function is devised to make the RNN prediction more accurate for larger changes in HMT, i.e., when dY is large. For instance, more than 20° C. may be considered to be large in blast furnace operation. Another threshold value may be configured, for example, above which is considered to be large.

Referring back to FIG. 2, at 210, the relationship between state variables and hot metal temperature (HMT) data points is learned. For example, the RNN-LSTM model that is set up or generated at 208 is trained using the process data and the HMT data including the interpolated HMT data. The RNN-LSTM model learns dY (difference HMT).

In one embodiment, predicting the HMT for future state includes guided cruise of DL, autonomous prediction of unknown HMT using previously predicted HMT data, and blind forecasting of HMT.

At 212, guided cruise of DL using HMT measurement data and interpolated HMT data is performed. In this processing step, LSTM is guided by the measurement data:

$$Y_{t+1}=w_{t+1}\tilde{Y}_{t+1}+(1-w_{t+1})Y^*_{t+1}$$

$$w_t=\alpha[1-\tan h(\beta(T-t))]$$

Where $Y^*_{t+1}$ is the RNN-LSTM prediction, i.e., $Y^*_{t+1}=Y_t+d\tilde{Y}_{t+1}$, $\overline{Y}_{t+1}$ is interpolated value, and T is the time of the next measurement. The parameters, $\alpha$ and $\beta$, determine how close the reconstructed trajectory, $Y_{t+1}$, should be to the linear interpolated estimate, $\overline{Y}_{t+1}$. The first parameter, $\alpha \in (0,1)$, determine the relative importance between $\overline{Y}$ and $Y^*$, and the second parameter, $\beta$, decides the timescale of the weight function, e.g., for a large $\beta$, the weight is almost zero in most of the time and becomes $w=\alpha$ very rapidly only around T, while a small $\beta$ makes the weight, w, change more gradually in time. The parameters, $\alpha$ and $\beta$ are configurable. Therefore, in one embodiment, more weight is placed on interpolated data closer to the measurement, while more weight is placed on the RNN-LSTM prediction away from the measurement. In one embodiment, this guided cruise of DL is performed with the past HMT data up to the last known HMT measurement. When (e.g., responsive to, or after) a new HMT measurement is acquired, using this new data as a part of training data, the DL model is retrained.

At 214, autonomous prediction of unknown HMT using previously predicted HMT data is performed. Autonomous prediction allows for making a prediction without having the observation data at every time step. In this autonomous prediction process, the RNN-LSTM prediction in the previous time step is used as input. For example, in the autonomous prediction mode, 1 time step prediction is performed as $d\tilde{Y}_{T+n}=LSTM(Y^*_{T+n-1}, X_{T+n-1}, U_{T+n-1})$, in which $X_{T+n-1}$ is the observation of the process variables, $U_{T+n-1}$ is the control variable, e.g., raw material charge rate, blast air volume, and blast air humidity, $Y_T$ is the last HMT measurement, $Y^*_{T+n-1}$ is the RNN-LSTM prediction from $Y_T$ computed recursively, e.g., $Y^*_{T+1}=Y_T+LSTM(Y_T, X_T, U_T)$, $Y^*_{T+2}=Y^*_{T+1}+LSTM(Y^*_{T+1}, X_{T+1}, U_{T+1})$, . . . , $Y^*_{T+n-1}=Y^*_{T+n-2}+LSTM(Y^*_{T+n-2}, X_{T+n-2}, U_{T+n-2})$. The autonomous prediction is performed from the time of the last HMT measurement to the current time.

At 216, blind forecasting of HMT is performed. The blind forecasting is performed to make a forecast from the current time. In this forecasting, a prediction is made for a future period, for example, n-time step ahead or forward prediction such as a 1-hour ahead or forward prediction is performed without providing any observation data. For example, suppose that the current time is 1:00 and the last HMT measurement time is T=0:00. Then, the autonomous prediction is made from 0:00 to the current time, 1:00, by using the observations of the process variables, $X_t$, and the past control actions $U_t$. As an example, it is assumed that the time step size is 20 minutes. Then, the current time can be denoted by T+3 and we have the autonomous model prediction, $Y^*_{T+3}=Y_T+\Sigma_{i=1}^3 d\tilde{Y}_{T+i}$, and the observation of process variables, $X_{T+3}$. In the blind forecast mode, the HMT prediction is updated by fixing X to be the last known value and the future U according to a desired control strategy, i.e., $$Y^*_{T+4}=Y^*_{T+3}+LSTM(Y^*_{T+3},X_{T+3},U_{T+3}), Y^*_{T+5}$$
$$=Y^*_{T+4}LSTM(Y^*_{T+4},X_{T+3},U_{T+4}), \text{ and}$$
$$Y^*_{T+6}=Y^*_{T+5}+LSTM(Y^*_{T+5},X_{T+3},U_{T+5}).$$

In one embodiment, retraining is performed for every new HMT measurement, i.e., the actual HMT data. For instance, receiving the actual HMT measured data may automatically trigger the retaining of the model (e.g., the deep learning neural network model self-retraining or retraining itself, responsive to receiving an actual HMT measured data).

At 218, the forecasted HMT data at 216 is sent or transmitted to the process control system and/or to a control operator.

At 220, the control system in response to receiving the forecasted HMT data performs a control action. Examples of the control action may include adding humidity content or oxygen enrichment of blast air and increasing iron ore to coke ratio, for instance, controlling the input content amount by automatically controlling (closing or opening) an input conduit.

Figure 7:
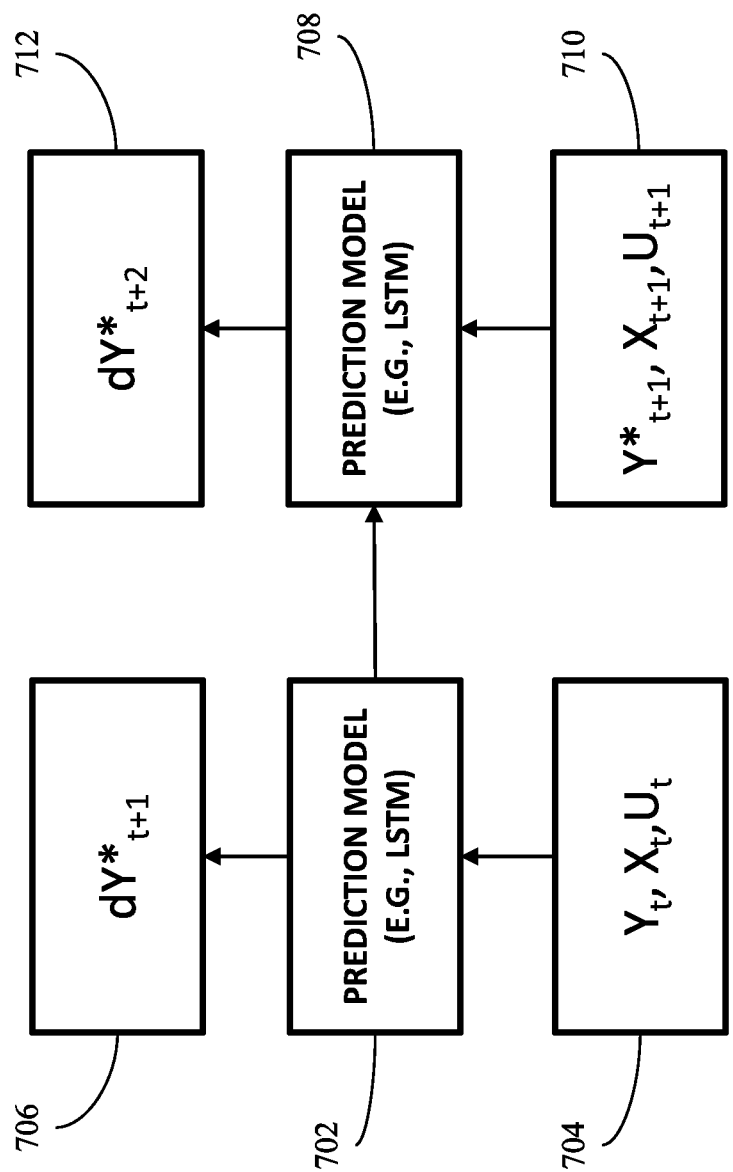
FIG. 7 shows a block diagram showing a deep neural network model for predicting future HMT difference in one embodiment.

FIG. 7 is a diagram showing an autonomous prediction in one embodiment. The prediction model, e.g., an LSTM network model 702 receives input data 704 associated with time t and outputs a prediction 706 of a delta value of the state variable for time t+1, for example, delta HMT at time t+1. The input data 704 is the actual measured data at time t. The predicted t+1 time data and process data measurements 710 are input to the prediction model 708, and the model 708 outputs a prediction 712 of a delta value of the state variable for time t+2, for example, delta HMT at time t+2. The LSTM model shown at 702 may be the same as the LSTM model shown at 708.

Figure 8:
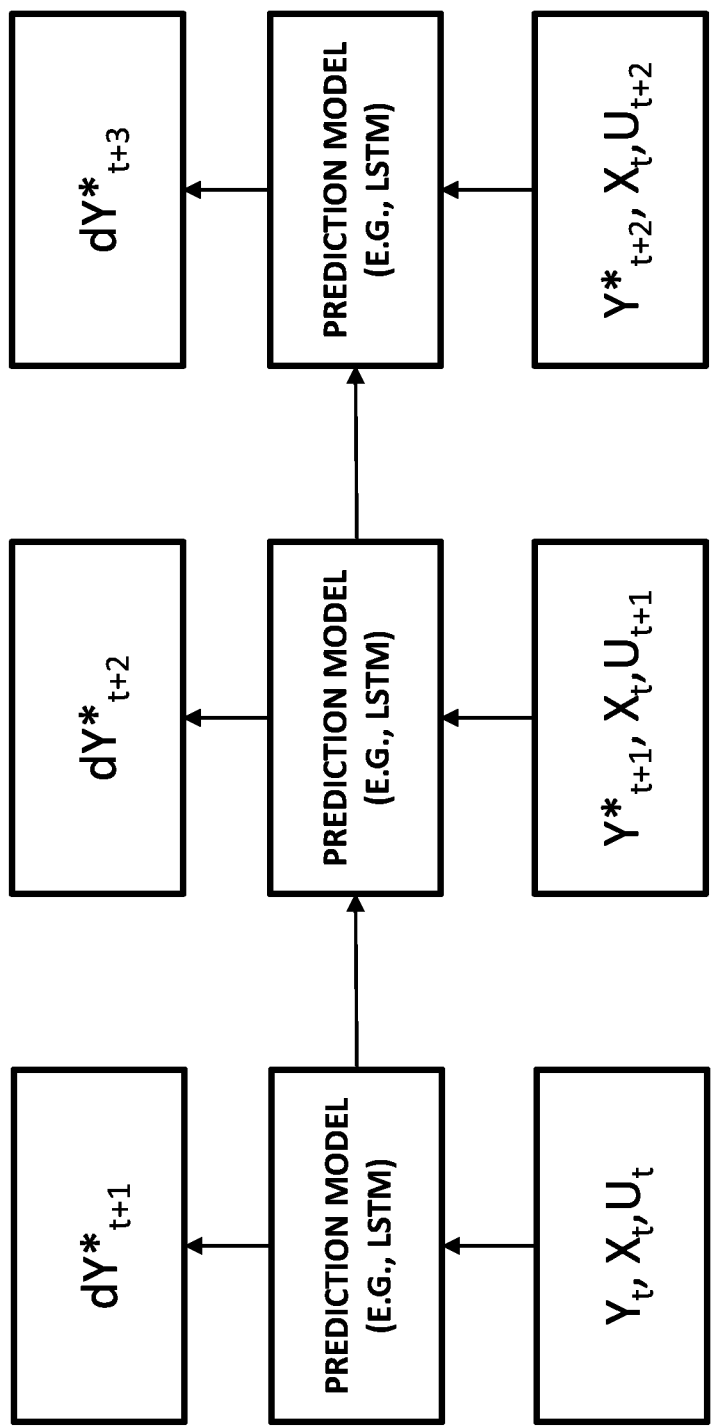
FIG. 8 is a diagram showing LSTM deep learning prediction model in one embodiment.

FIG. 8 is a diagram showing a blind forecast modeling in one embodiment. The figure illustrates a 3-step ahead or forward prediction as an example; for example, if 20-minute time interval is used for each time step, 3-step ahead prediction produces a forecast or prediction for 1-hour ahead of time t. For instance, $Y_{t+1\ hour} = Y_t + dY^*_{t+1} + dY^*_{t+2} + dY^*_{t+3}$, where $dY^*_{t+1}$, $dY^*_{t+2}$, and $dY^*_{t+3}$ are predicted delta values, and $Y_t$ is the actual measured data. The model runs are performed sequentially, for example, using as input a previously predicted output at the previous future time step run. Y here represents the state variable being predicted, e.g., HMT. X here represents other features or variables used by the model, such as the temperature and pressure measurements from sensors. U here represents the control actions, such as the raw material charging rate, blast air humidity, blast air volume, and so on. The model learns the relationship between Y, X, and U values.

Figure 9:
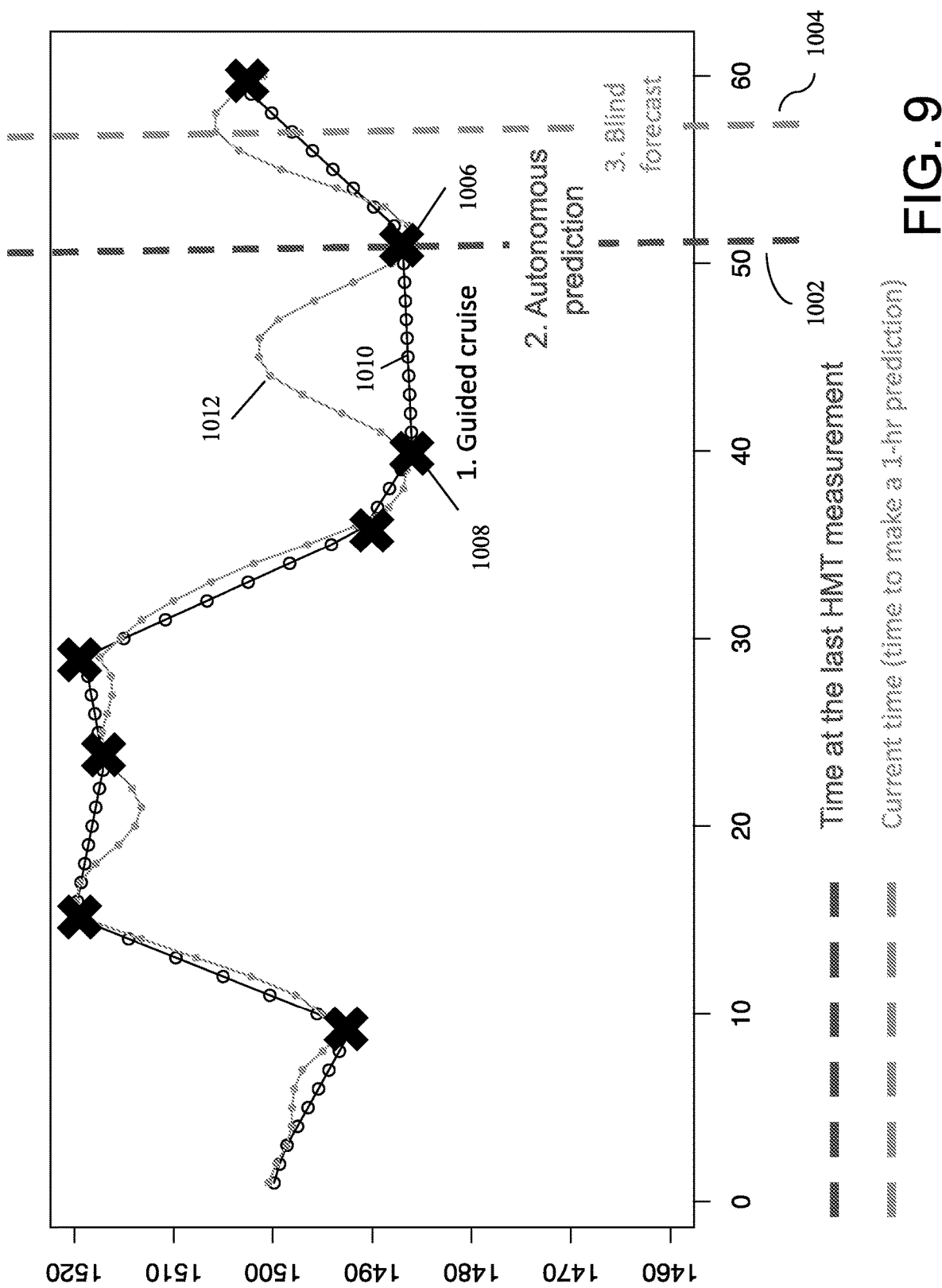
FIG. 9 is a graphical diagram illustrating an example of forecasting of a state variable ahead in time in one embodiment.

FIG. 9 is a graphical diagram illustrating an example of forecasting of a state variable (e.g., HMT) ahead in time in one embodiment. The point in time shown at 1002 represents the time at the last HMT measurement. The point in time shown at 1004 represents the current time, for example, the time to make a 1-hour ahead or forward prediction. At the time shown at 1002, when that HMT measurement is received, the prediction model (e.g., LSTM model) is retrained by guided cruise technique described above. The LSTM model is guided by the measurement data, in that the interpolated data (shown by data points along the line 1010) between that last measurement data 1006 and the previous measurement data 1008 are generated and combined with the previously predicted data (predicted data by autonomous prediction shown along the curve 1012) to retrain the model. In one embodiment, the training data from the time of the measured data point at 1008 to the time of the measured data point at 1006, are generated as the weighted average or weighted combination of the interpolated data 1010 and the predicted data 1012 between those two measured data points.

From the time 1002 of the last HMT measurement, an autonomous prediction mode takes place where 1-time step prediction is performed without a forward HMT measured data. For instance, self-generated HMT is used as input to LSTM model to generate a next time step prediction. To generate a prediction data for the current time shown at 1004, a blind forecast mode is performed. The blind forecast mode performs the 1-step prediction of the autonomous prediction mode, n-times to forward to the current time. For instance, if the time duration between the time at the last HMT measurement 1002 and the current time 104 is 1 hour, and if the 1-step time is 20 minutes, then 3-step predictions are performed, for instance, as shown in FIG. 8. In performing the blind forecast mode, in one embodiment, the values of other features used in the model, such as pressure and temperature observations from sensors, may be set to the last known values.

In one embodiment, the long short-term memory (LSTM) network is modeled. The LSTM model of the present disclosure in one embodiment mitigates problems of rapidly degrading accuracy as the time lag increases, and being able to account for the trajectory of a dynamical system, which may occur in other learning algorithms. The LSTM model of the present disclosure in one embodiment is a latent space model that incorporates the past trajectory of a blast furnace, and provides for the continuous estimation of the current state of the blast furnace and prediction for the future.

Deep learning (DL), a type of machine learning, is a computational model composed of multiple processing layers to learn representations of data with multiple levels of abstraction. Deep learning methods have been utilized in speech recognition, visual object recognition, object detection and other domains such as drug discovery and genomics. A recurrent neural network (RNN) is a type of neural network in which the neuron feeds back information to itself, in addition to processing to the next neuron, and is capable of learning long-term dependencies, e.g., time-series data. An RNN can learn long-term dependencies, but has difficulties in learning to store information for a long duration. Long short-term memory (LSTM) networks augment the RNN network with an explicit memory through a built-in memory cell. In the present disclosure, LSTM technology is utilized to develop a predictive model for a complex manufacturing process, providing for an LSTM algorithm and/or architecture for discovering a long term dependency in the process.

Figure 10:
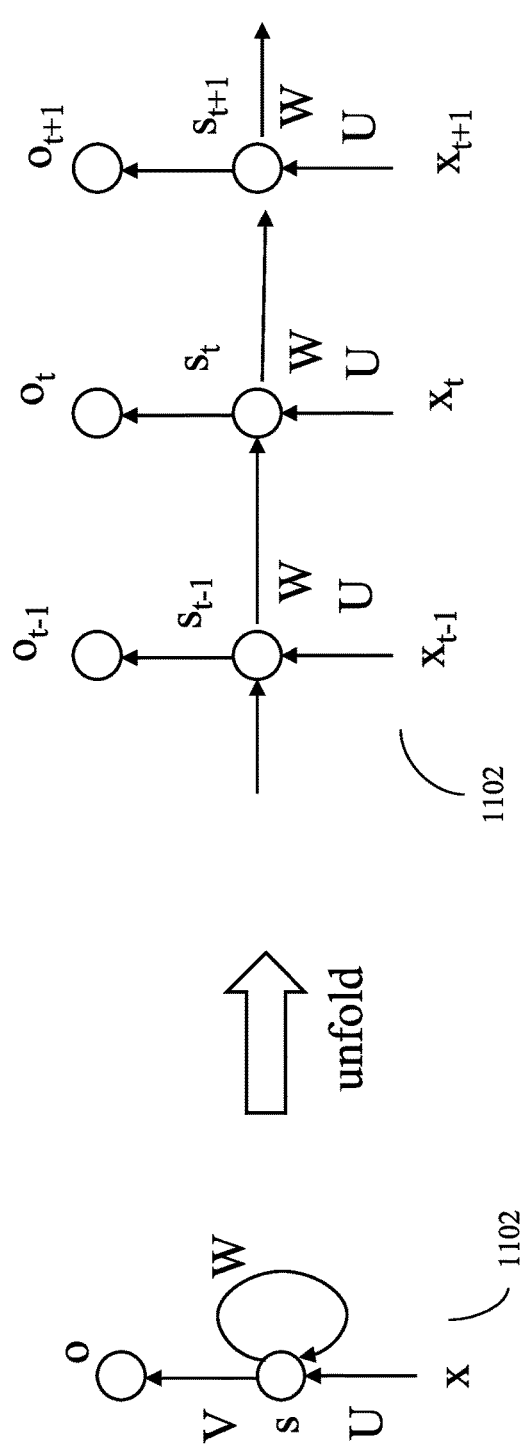
FIG. 10 illustrates Recurrent Neural Network (RNN) structure in one embodiment.

FIG. 10 illustrates RNN in one embodiment. The left side 1102 of FIG. 10 shows the structure of a RNN. For a specific time period of modeling, a RNN model captures the relationship, called state s, between input x, output o and the state s in previous time period. The parameter set for the links between x and s denotes U, and the parameter set for the links between s and o denotes V. The parameter set for the links between previous state and current state denotes W. If the RNN structure is unfolded to show the relationship between states in different time periods, it looks like the structure 1104 on right side of FIG. 10. The state at time t+1, $s_{t+1}$, captures the relationship between the state at time t, $s_t$, input $x_{t+1}$ and output $o_{t+1}$.

Figure 11:
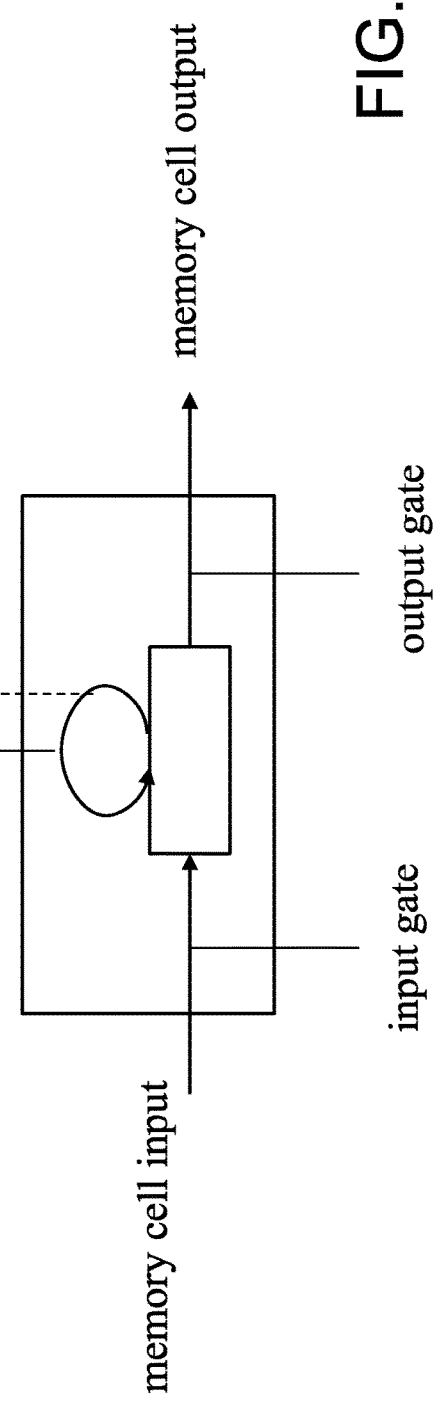
FIG. 11 is a block diagram showing a memory cell of an LSTM network in one embodiment.

FIG. 11 is a block diagram showing a memory cell of an LSTM network in one embodiment. Since an LSTM uses data from previous time steps, the amount of data used by a LSTM model may be very large. In order to handle the data size problem in a computer system, the memory cells screen the amount of data to be used by controlling three types of gates. An input gate conditionally determines which input data to use in the LSTM model. A forget gate conditionally determines which information (data) it learned from past time periods is going to be used in the memory cell of current time step. An output gate conditionally determines which data it is currently using in the memory cell, to output to the memory cell of next time period.

Figure 12:
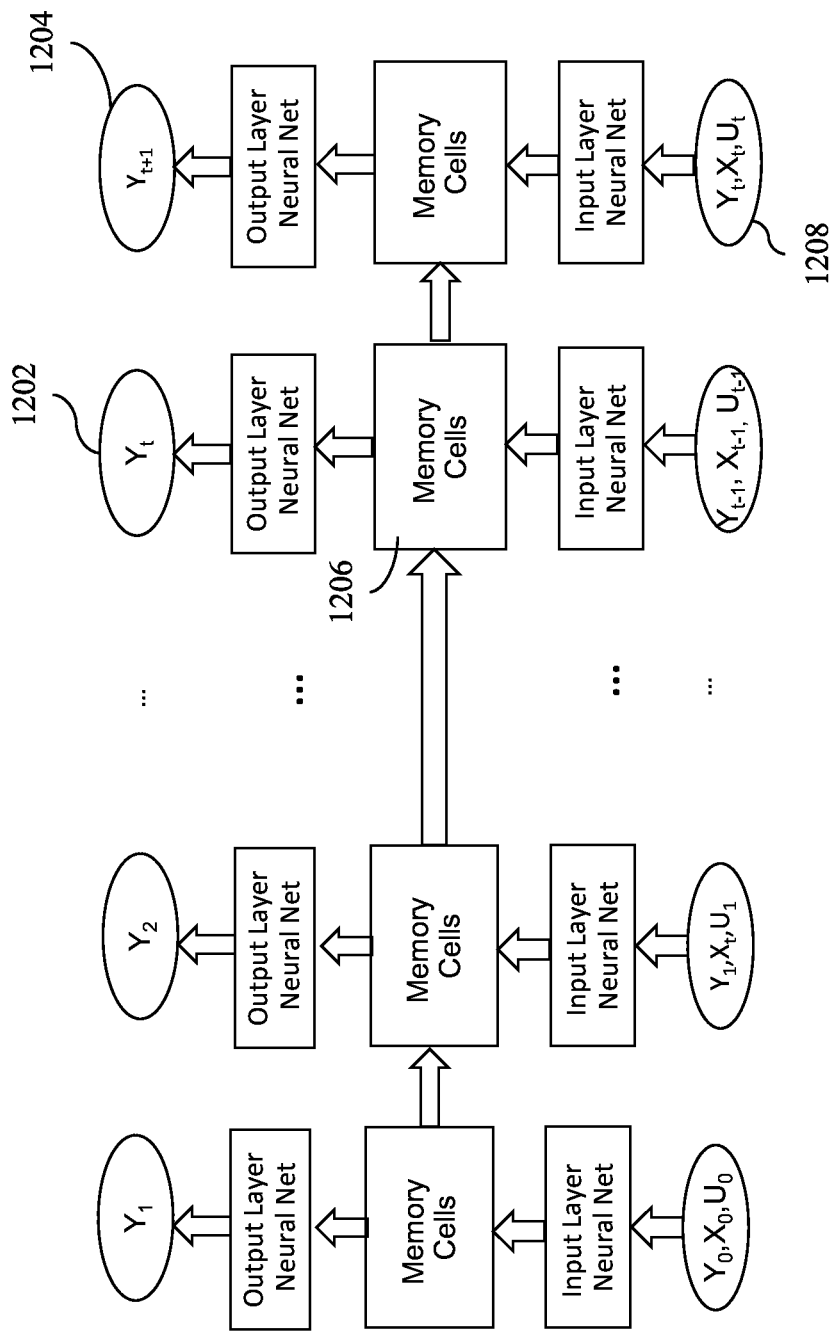
FIG. 12 is an architectural diagram showing an example long short-term memory (LSTM) network in one embodiment.

FIG. 12 is an architectural diagram showing an example long short-term memory (LSTM) network in one embodiment. Here, $Y_t$, e.g., 1202, denotes a vector of the target variables at time t. $X_t$ and $U_t$ are the state variables and the control variables at time t. At each time step t, LSTM updates its memory cell, e.g., 1206 (example shown in FIG. 11), and makes a prediction at the next time step, $Y_{t+1}$, e.g., 1204, from the current observations $Y_t$, state variables, $X_t$, and the control actions, $U_t$, e.g., 1208. Because the past information is stored in the memory cells, the previous observations, e.g., $Y_{t-1}$, $Y_{t-2}$, $X_{t-1}$, $X_{t-2}$, $U_{t-1}$, $U_{t-2}$, are not used in the prediction at time t.

A long short-term memory (LSTM) model in one embodiment is a recurrent neural network (RNN). Information learned is passed from one step of the network to the next step. The long short-term memory (LSTM) model connects previous information to the present state, and learns long-term dependencies (time-series data). A response time of control actions has wide variations, e.g., from a few seconds to hours. For instance, the state variables that change as a consequence of the control actions performed on the blast furnace, may be reflected in data sensed few seconds to hours after the time of the control action.

The LSTM model in one embodiment predicts a future state for a state variable as a function of the previous states of the state variable and other variables involved in the process. For instance, $y_{t+1}=f(y_t, y_{t-1}, y_{t-2}, \ldots, x_t, x_{t-1}, x_{t-2}, \ldots, u_t, u_{t-1}, u_{t-2}, \ldots, u^*_{t+1})$, where t represents a point in time (time unit), y represents the response variable (also called target variables) that are intended to be predicted, x represents uncontrollable state variables (also called observed variables), and u represents controllable state variables (also called control variables).

The future state of a state variable is determined, for example, as follows: $y_{t+1}=f(Y_t^-, X_t^-, U_t^-, U_{t+1}^+)$,
where t represents point in time, y represents the state variable whose future state is being predicted, $Y_t^-$ represents a vector of response variables from past to present time, $X_t^-$ represents a vector of uncontrollable state variables from past to present time, $U_t^-$ represents a vector of controllable state variables from past to present time, and $U_{t+1}^+$ represents a vector of controllable state variable for the future time,
where
target variable (y): $Y_t^-=\{y_t, y_{t-1}, \ldots, y_{t-n}\}$, n representing number of past time steps,
state variables: $X_t^-=\{x_t, x_{t-1}, \ldots x_{t-n}\}$,
control variables (past): $U_t^-=\{u_t, u_{t-1}, \ldots u_{t-n}\}$
control variables (future): $U_{t+1}^+=\{u_{t+1}, u_{t+2}, \ldots u_{t+M}\}$, M representing number of future time steps for prediction.

FIG. 6 is a diagram illustrating a method of controlling a manufacturing process occurring in a blast furnace in one embodiment of the present disclosure. At 602, manufacturing process data associated with a blast furnace is received. The manufacturing process data includes state variables and control variables used in operating the blast furnace, the state variables comprising at least a hot metal temperature (HMT) and other state variables, wherein the manufacturing process data comprises a plurality of measured HMT at different time points, of a product continuously produced in the blast furnace. At 604, imputed HMT is generated by interpolating the measured HMT. For instance, HMT is imputed that correspond to the time points between the times of the measure HMTs. At 606, HMT gradients are generated based at least on the imputed HMT. For instance, the difference between an imputed HMT at a time point and the next imputed HMT at the next time point is determined over a plurality of time points as a time series data. At 608, a causal relationship is defined between the other state variables and the HMT gradients. The relationship is generated as a neural network model. At 610, the neural network model is trained using as training data, a weighted combination of the imputed HMT up to a last known measured HMT and predicted HMT up to the last known measured HMT. At 612, the trained neural network model is run to predict a current point in time value for the HMT, in which no measured HMT for the current point in time is available. The trained neural network model predicts the HMT corresponding to a time period starting from the time of the last measure HMT data point for a number of time periods until the number of time periods advances to the current point in time and uses the predicted HMT corresponding to each of the number of time periods to predict the current point in time value for the HMT. At 614, the current point in time value for the HMT is transmitted to a controller coupled to the blast furnace, to trigger a control action to control a manufacturing process occurring in the blast furnace. The product, for example, includes pig iron and the manufacturing process includes a continuous blast furnace operation. In one embodiment, the neural network model includes a long short-term memory network. The manufacturing process data may be stored as a time series data. In one embodiment, the neural network model is autonomously retrained responsive to receiving a new measured HMT, using the new measured HMT as the last known measured HMT. In one embodiment, the plurality of measured HMT at different time points includes a plurality of measured HMT measured at irregular time intervals.

Figure 13:
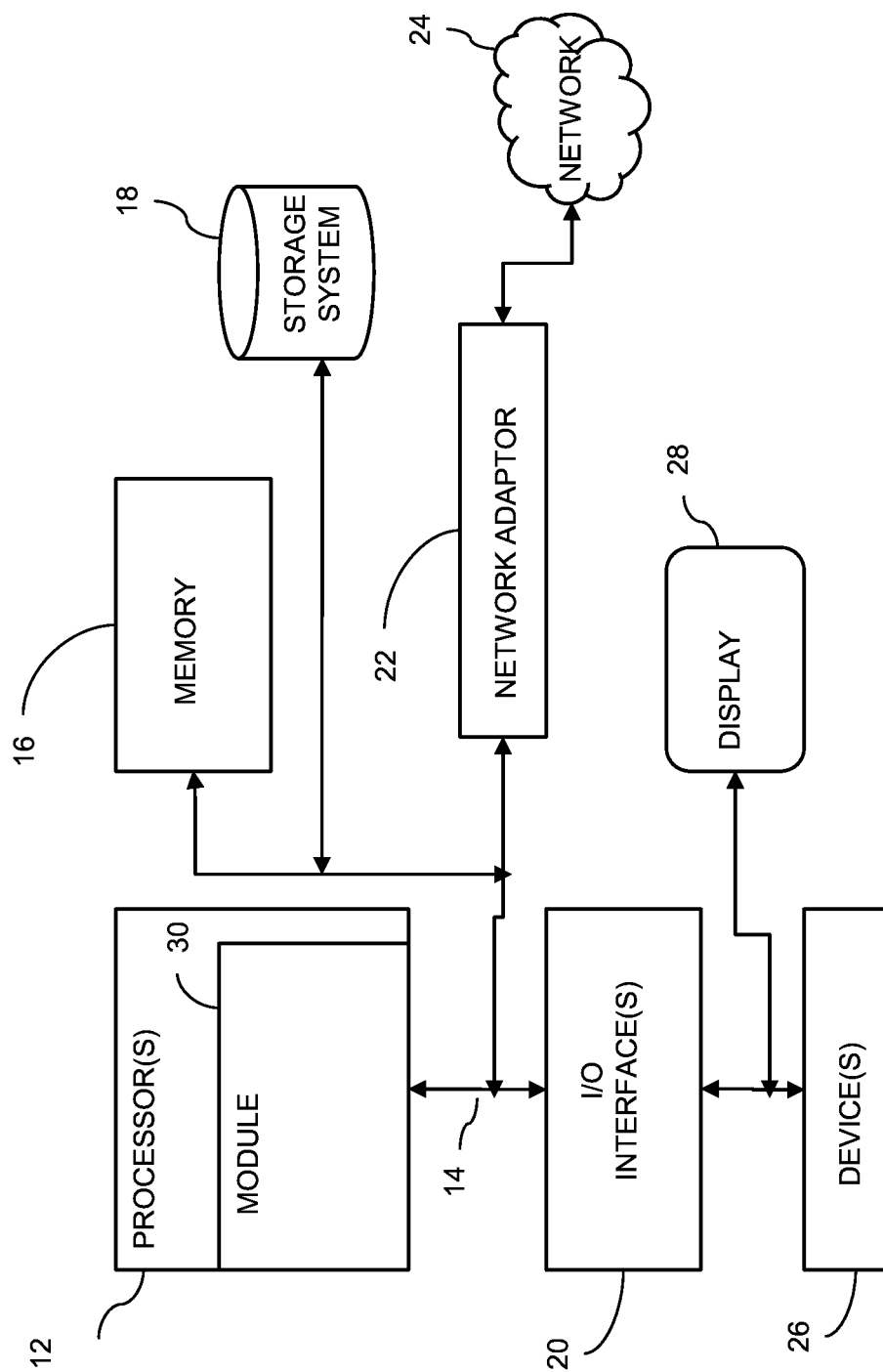
FIG. 13 illustrates a schematic of an example computer or processing system that may implement a control system in one embodiment of the present disclosure.

FIG. 13 illustrates a schematic of an example computer or processing system that may implement a control system in one embodiment of the present disclosure. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 13 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include a predictive model module 30 that performs the methods described herein. The module 30 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

We claim:

1. A blast furnace control system, comprising:
a storage device storing a database of manufacturing process data associated with a blast furnace;
a hardware processor coupled to the storage device and configured to receive the manufacturing process data, the manufacturing process data comprising at least state variables and control variables used in operating the blast furnace, the state variables comprising at least a hot metal temperature (HMT) and other state variables, wherein the manufacturing process data comprises a plurality of measured HMT at different time points, of a product continuously produced in the blast furnace, the hardware processor further configured to:
generate imputed HMT by interpolating the plurality of measured HMT;
generate HMT gradients over time at least based on the imputed HMT;
define a causal relationship between the other state variables and the HMT gradients, the relationship generated as a neural network model;
train the neural network model using as training data, a weighted combination of the imputed HMT up to last known measured HMT and predicted HMT up to the last known measured HMT;
run the trained neural network model to predict a current point in time value for the HMT, in which no measured HMT for the current point in time is available, wherein the trained neural network model predicts the HMT corresponding to a time period starting from the time of the last measured HMT for a number of time periods until the number of time periods advances to the current point in time and uses the predicted HMT corresponding to each of the number of time periods to predict the current point in time value for the HMT; and
transmit the current point in time value for the HMT to trigger a control action, the control action including at least selectively opening a conduit to the blast furnace to control content amount of input to the blast furnace.

2. The system of claim 1, wherein the product comprises pig iron.

3. The system of claim 1, wherein the neural network model comprises a long short-term memory network.

4. The system of claim 1, wherein the blast furnace comprises a plurality of sensors taking measurements associated with the other state variables and the control variables, wherein the database of manufacturing process data stores the measurements as a time series data.

5. The system of claim 1, wherein the hardware processor autonomously retrains the neural network model responsive to receiving a new measured HMT, using the new measured HMT as the last known measured HMT.

6. The system of claim 1, wherein the manufacturing process includes a continuous blast furnace operation.

7. The system of claim 1, wherein the plurality of measured HMT at different time points comprises a plurality of measured HMT measured at irregular time intervals.

8. A computer program product for controlling a manufacturing process in a blast furnace, the computer program product comprising a non-transitory computer readable storage medium having program instructions embodied therewith, the program instructions readable by a device to cause the device to perform a method comprising:

receiving manufacturing process data associated with a blast furnace, the manufacturing process data comprising at least state variables and control variables used in operating the blast furnace, the state variables comprising at least a hot metal temperature (HMT) and other state variables, wherein the manufacturing process data comprises a plurality of measured HMT at different time points, a product of continuously produced in the blast furnace;

generating imputed HMT by interpolating the measured HMT;

generating HMT gradients based on at least the imputed HMT;

defining a causal relationship between the other state variables and the HMT gradients, the relationship generated as a neural network model;

training the neural network model using as training data, a weighted combination of the imputed HMT up to a last known measured HMT and predicted HMT up to the last known measured HMT;

running the trained neural network model to predict a current point in time value for the HMT, in which no measured HMT for the current point in time is available, wherein the trained neural network model predicts the HMT corresponding to a time period starting from the time of the last measure HMT data point for a number of time periods until the number of time periods advances to the current point in time and uses the predicted HMT corresponding to each of the number of time periods to predict the current point in time value for the HMT; and transmitting the current point in time value for the HMT to trigger a control action to control a manufacturing process occurring in the blast furnace, the control action including at least selectively opening a conduit to the blast furnace to control content amount of input to the blast furnace.

9. The computer program product of claim 8, wherein the product comprises pig iron.

10. The computer program product of claim 8, wherein the neural network model comprises a long short-term memory network.

11. The computer program product of claim 8, wherein the manufacturing process data is stored as a time series data.

12. The computer program product of claim 8, further comprising autonomously retraining the neural network model responsive to receiving a new measured HMT, using the new measured HMT as the last known measured HMT.

13. The computer program product of claim 8, wherein the plurality of measured HMT at different time points comprises a plurality of measured HMT measured at irregular time intervals.

* * * * *